US007811306B2

(12) United States Patent
Lyapko

(10) Patent No.: US 7,811,306 B2
(45) Date of Patent: Oct. 12, 2010

(54) MODULAR APPLICATOR FOR USE IN REFLEXOTHERAPY

(76) Inventor: Nicolai Grigorievich Lyapko, 8, m-n Sonyachny, app. 21, Krasnogorivka, Marjinsky rajon, Donetskoy obl., 85402 (UA)

( * ) Notice: Subject to any disclaimer, the term of this patent is extended or adjusted under 35 U.S.C. 154(b) by 1040 days.

(21) Appl. No.: 10/312,744

(22) PCT Filed: Jun. 27, 2001

(86) PCT No.: PCT/UA01/00019

§ 371 (c)(1),
(2), (4) Date: Dec. 27, 2002

(87) PCT Pub. No.: WO02/03906

PCT Pub. Date: Jan. 17, 2002

(65) Prior Publication Data

US 2004/0254509 A1 Dec. 16, 2004

(30) Foreign Application Priority Data

Jun. 29, 2000 (UA) .............................. 2000063821

(51) Int. Cl.
*A61B 17/00* (2006.01)

(52) U.S. Cl. ...................................................... 606/204

(58) Field of Classification Search ................. 606/186, 606/189, 204, 201, 151, 157, 232, 54, 1; 604/27, 46; D24/200; 24/661, 662
See application file for complete search history.

(56) References Cited

U.S. PATENT DOCUMENTS

| | | | | | |
|---|---|---|---|---|---|
| 1,352,153 | A | * | 9/1920 | Smith et al. | 24/676 |
| 3,034,507 | A | * | 5/1962 | McConnell et al. | 604/46 |
| 3,072,122 | A | * | 1/1963 | Rosenthal | 604/46 |
| 3,074,403 | A | * | 1/1963 | Cooper et al. | 604/46 |
| 5,250,067 | A | * | 10/1993 | Gelfer et al. | 606/189 |
| 5,487,726 | A | * | 1/1996 | Rabenau et al. | 604/46 |
| 5,938,684 | A | * | 8/1999 | Lynch et al. | 606/204 |

FOREIGN PATENT DOCUMENTS

JP 2000225171 A * 8/2000

* cited by examiner

*Primary Examiner*—Anhtuan T Nguyen
*Assistant Examiner*—Elizabeth Houston
(74) *Attorney, Agent, or Firm*—Weiner & Burt, P.C.; Irving M. Weiner; Pamela S. Burt

(57) ABSTRACT

A modular applicator for use in reflexotherapy, for stimulating specific reflex points on the surface of a human body. The applicator has an elastic base member and modules. Each module is made from metal and provided with an elastic base member which allows a cheaper manufacture, ensures a firm brace between needles and fastening member, eliminates breaking and provides greater comfort to users.

5 Claims, 20 Drawing Sheets

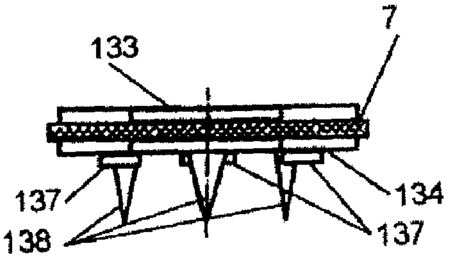
Fig. 88
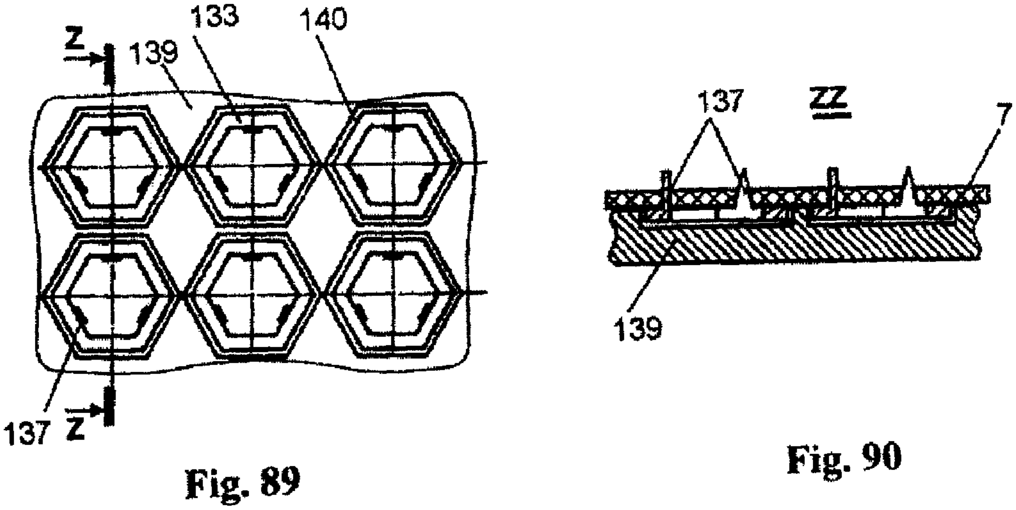
Fig. 89
Fig. 90
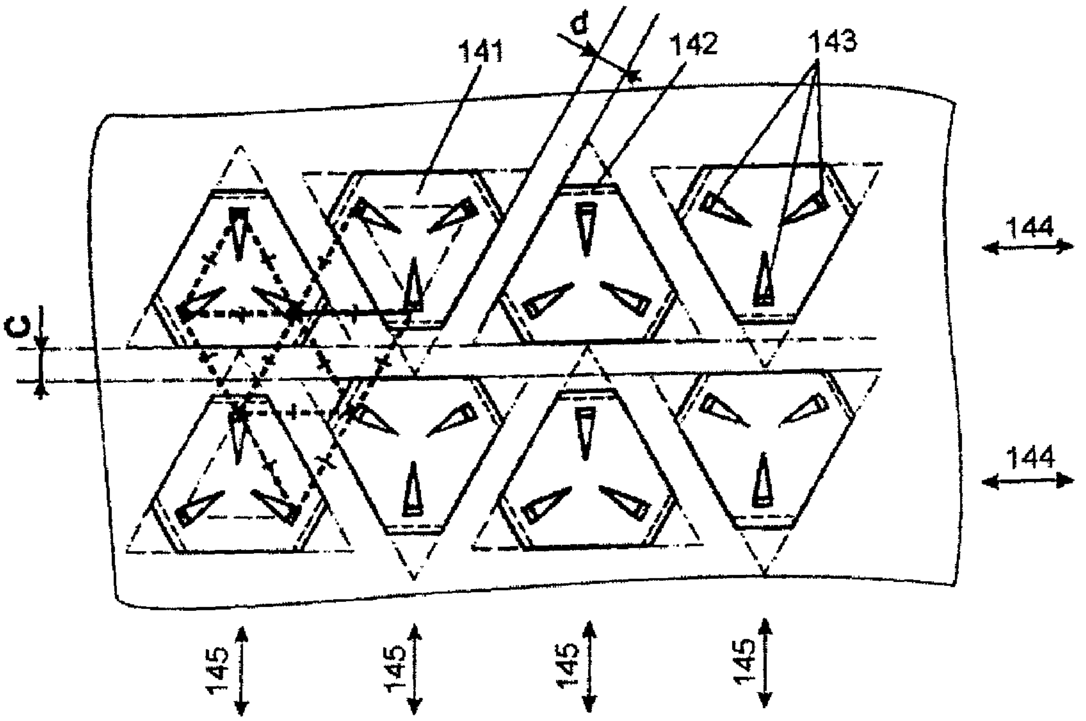
Fig. 91

MODULAR APPLICATOR FOR USE IN REFLEXOTHERAPY

FIELD OF INVENTION

The invention relates to devices used in physiotherapy, and particularly in reflexotherapy with the aim of stimulating specific reflex points on the surface of a human body, and particularly to modular applicators, and may be used at medical and athletic institutions, as well as under home conditions for reflexotherapy, particularly in case of the need to provide action of needles on the user's epidermis when practicing exercises that involve long amplitudes of swings, bends, and torsions of individual body members.

BACKGROUND OF THE INVENSION

The closest device to the proposed applicator comprises a modular applicator having an elastic base member and unit-cast plastic modules fastened therein, each module having a head member and needles that are made integrally therewith and disposed in perpendicular relationship thereto, said head member being provided with at least one opening to accommodate a fastening member (SU,A,986422).

Manufacture of modules from plastic and resulting utilization of a comparatively expensive molding technology for such manufacture cause an insufficiently firm brace between the needles and the module head member, and hence the possibility of their breaking off, comparatively high module massiveness, insufficiently thin and sharp needles, and relatively discomfort perception of applicators by users. Manufacture of modules from plastic also results in impossibility of providing such modules with fastening members made integrally with said modules, since such members would either break off during their bending to the surface of the applicator base member or would not provide sufficiently firm brace between the module and this base member, which in turn causes the need to provide additional means, i.e. fastening members whose utilization results in a more complicated technology of modules fastening on the applicator base member and does not permit to mechanize this technology. In addition, manufacture of modules from plastic practically eliminates the possibility of applying metal coatings either to the whole modules or to needles, since it involves certain complications and difficulties; coatings applied to plastic are not durable and come off from said plastic, thereby eliminating the possibility of action in the process of reflexotherapy with galvanic currents that might be generated between needles or modules made of or coated with dissimilar metals. This also eliminates the possibility of electrophoresis. The above two factors cause the restriction of reflexotherapy capabilities.

BRIEF DISCLOSURE OF THE INVENTION

The main object of the invention consists in improving the modular applicator by way of making each module from metal and providing each module with at least one fastening member that is made integrally with said head member and disposed in perpendicular relationship thereto, which fact provides the possibility of manufacturing said modules with the use of a cheaper method, i.e. stamping; eliminates the need of in separate devices, i.e. fastening members; ensures a firm brace between the needles and fastening members, and head members of modules, and eliminates their breaking off; allows the modules to be made less massive, and the needles thinner and sharper; provides a more comfort perception of needles action by users; simplifies the technology of modules fastening on the applicator base and permits to mechanize this process; causes the possibility of making modules from various metals and applying various firm coatings of various materials to the modules.

The object set forth is achieved by that in a modular applicator comprising an elastic base member and modules fixed thereon, each module being provided with a head member with at least one needle perpendicular thereto, according to the invention, modules are made metallic, and each of said modules is provided with at least one fastening member made integral with the module head member and bent away therefrom in either the same or opposite direction with respect to needle/needles, each fastening member or each needle together with said fastening member being passed through the applicator base member, and each fastening member being bent away to the surface thereof.

Manufacture of metallic modules makes it expedient to produce fastening members integral with modules head members, while using stamping instead of molding (e.g. by cutting out fastening members and needles in the body of the module head member, followed by bending them away from said head member). Metallic needles and fastening members made by stamping and being integral with the head member are firmly connected to the head member; therefore they do not break off from said head member during bends in the process of manufacture of modules and fastening them on the applicator base member, as well as under operational loads. The use of stamping allows modules to be less massive, needles thinner and sharper, and head member thinner. The action of metallic needles is better perceived by users. In addition, all this simplifies the technology of fastening modules to the applicator base member, since in this case the only thing needed is to pass fastening members through the base member and to bend them away to the surface thereof; such technology can be mechanized by way of placing modules in a preset relationship with respect to the applicator base member, and by using rollers for the purpose of bending fastening members away to the base member surface. Making modules metallic also provides for the possibility of either making said modules from dissimilar metals or applying various strong coatings (single or multilayer, solid or partial) made of various metals to the modules, thereby expanding the range of reflexotherapy (along with mechanical irritation of user's epidermis, there takes place the action of galvanic microcurrents between needles or modules, as well as electrophoresis with transfer of required microelements from the modules to the user's body).

Fastening members may be made in the form of at least one set of circumferentially disposed lobes made by drawing with a conical punch, thereby causing a compact arrangement of several fastening members, ensuring a higher strength of brace between the modules and the applicator base member, and leaving a larger area for arrangement of needles; it however complicates the technology of making modules and fastening them to the applicator base member.

Both fastening members and needles may be shaped as triangular dents cut out in the body of the head member at a distance from periphery thereof along two sides of a dent, and bent away along the third side thereof at the right angle from the head member either in the same or in opposite directions.

Fastening members and/or needles may be shaped as triangular dents cut out in the body of the head member starting from periphery thereof along one side of a dent, and bent away from the head member around the second side either in the same or in opposite directions, the third side of a dent being formed by a section of the peripheral edge of the head member.

Shaping both fastening members and needles as above dents, and particularly with the same sizes, allows similar operations for making both fastening members and needles on the same equipment (blanking-and-bending dies) to be used, and the number of process operations to be reduced, thereby considerably simplifying the technology of modules manufacture. The first option of making dents is somewhat more complicated but more reliable, while the second one is simpler but less reliable. Making the dents of the same module with the use of two options permits to produce, without any increase in the head member sizes, more fastening members and/or needles. Bending away all the dents, i.e. those performing the functions of needles and fastening members, in the same direction, simplifies the manufacture of modules but requires passing all the dents through the applicator base member, thereby decreasing the strength thereof; in addition, the loads during applicator utilization are taken only by fastening members rather than by the head member, thereby causing the possibility of breaking the fastening members off from the head member or weakening the brace between the module and applicator base member. Bending the dents away in opposite directions somewhat complicates the manufacture of modules but requires passage through the applicator base member of only fastening members rather than all the dents; in addition, the loads during applicator utilization are taken by the whole head member rather than by fastening members.

The module may be made triangular, with rectilinear or concave curvilinear sides, and at least some needles or fastening members may be made as triangular dents formed by triangle apices bent away at the right angle.

It should be noted that triangles may be made equilateral or isosceles or scalene. Equilateral triangles provide uniform arrangement of needles over the flat base member, while isosceles or scalene triangles ensure uniform arrangement of needles over the curvilinear base member.

The module may be shaped as a rhomb, and at least a portion of needles or fastening members may be triangular dents formed by acute-angled rhomb apices bent away at the right angle.

The module may be made as a hexagon with two acute-angled apices, and at least a portion of needles or fastening members may be triangular dents formed by its acute-angled apices bent away at the right angle.

Making dents in the form of acute-angled apices of a geometrical figure increases the strength of brace between dents and the head member, and eliminates the operation of cutting dents in the head member body from the production process of module manufacture, however requiring availability of additional dents cut in the head member body since the dents shaped as apices of the above geometrical figures may function either as fastening members or needles Each module may be also shaped as a rectangle with triangular beams cut therein and protruding outwards on two opposite sides thereof, said beams being disposed closely to one another, and at least a portion of needles or fastening members may be shaped as triangular dents formed by these beams or end portions thereof, that are bent away from the module head member in opposite directions, or by end members of said beams, bent away in the same direction.

In addition, each module may be shaped as a rectangle with triangular beams cut therein and protruding outwards on two opposite sides thereof, said beams being disposed in spaced relationship, and at least a portion of needles or fastening members may be shaped as triangular dents formed by these beams or end portions thereof.

Spaced arrangement of beams eliminates any possibility of cutting the applicator base member or passing said beams therethrough, i.e. eliminates separation of sections of the applicator base member in the points of modules placement from the rest of the base member, and hence ensures material savings between adjacent dents while increasing module dimensions and reducing applicator flexibility. Close arrangement of beams eliminates the possibility of cutting the applicator base member only in case of bending away said dents in opposite directions. Such arrangement of dents causes small sizes of modules and therefore an increased flexibility of the applicator.

Here, two dents may be provided on each of the opposite sides of the rectangle, two of them disposed along one diagonal being bent away to one side, and two of them disposed along the other diagonal, to the other side; alternatively, each of these sides of the rectangle may be provided with three dents, central dents being bent away to one side, and extreme dents, to the other side.

Some dents of the above figures may perform the function of needles, and others, the function of fastening members, thereby eliminating the need in additional dents.

It has to be noted that in a module provided with two dents on the opposite sides of a rectangle, such dents may be bent away either symmetrically with respect to the rectangle axis or symmetrically with respect to the center thereof. In the latter case, a more rigid bracing of modules to the applicator base member is provided.

In addition, the module may be shaped as a star with a polygonal or circular or oval base member, and at least three triangular beams protruding therefrom, said beams being disposed closely to one another, and at least a portion of needles or fastening members may be shaped as triangular dents formed by beam ends bent away from the head member in the same direction, or by these beams or end portions thereof, that are bent away in opposite directions.

Each module may be also shaped as a star with a polygonal or circular or oval base member, and at least three triangular beams protruding therefrom, said beams being disposed in spaced relationship, and at least a portion of needles or fastening members may be shaped as triangular dents formed by these beams or end portions thereof, that are bent away from the head member in the same or in opposite directions.

Such embodiment of the module provides a rigid brace between dents and the head member. Spaced arrangement of beams eliminates any possibility of applicator base member cutting with dents when passing the latter through the base member. Close arrangement of beams eliminates the possibility of cutting the applicator base member only in case of bending away the beams in the same direction, or in case of bending away said beams in the same direction but forming these dents by bent away end portions of beams. Embodiment of the star provided with three beams requires additional dents, while stars provided with more than three beams does not require such additional beams since some of the dents may serve as needles, and others, as fastening members.

The module may be shaped as a circle or an oval or a regular/irregular polygon provided with a central opening and a narrow bridge formed between periphery of the head member and said opening; at least a portion of needles or fastening members may be shaped as triangular beams protruding from the opening in the direction of the head member center and disposed in close relationship, at least a portion of needles or fastening members being shaped as triangular dents formed by these triangular beams or end portions thereof, bent away from the module head member in opposite directions, or by end portions of said beams, bent away in the same direction.

Each module may be also shaped as a circle or an oval or a regular/irregular polygon provided with a central opening and a narrow bridge formed between periphery of the head member and said opening, and triangular beams protruding from the central opening in the direction of the module head member center and disposed in a spaced relationship, at least a portion of needles or fastening members being shaped as triangular dents formed by these triangular beams or end portions thereof, bent away from the module head member in the same or opposite directions, or by end portions of said beams.

Such embodiment of modules ensures a considerable number of fastening members and/or needles at comparatively small sizes of modules and small mass thereof. Bending away of beams or end portions thereof, disposed in spaced or close relationship, in the same or opposite directions eliminates cutting the applicator base member by module dents, as has been stated above for other embodiments of modules.

Here, each module provided with a central opening may be made with triangular beams protruding outwardly from the head member periphery and disposed in close relationship, and equipped with additional triangular beams formed by end portions of these beams, bent away from the head member in one direction, or by these beams or end portions thereof, bent away in opposite directions, or each module may be provided with triangular beams protruding from the head member periphery and disposed in spaced relationship, and equipped with additional triangular beams formed by beams or end portions thereof, bent away from the head member in the same or opposite directions.

The above provision of the module with additional dents results in an increase in the number of needles and/or fastening members without increasing module dimensions. Bending away of protruding beams or end portions thereof, disposed in spaced or close relationship, in the same or opposite directions eliminates cutting the applicator base member by module dents, as has been stated above for other embodiments of modules.

Any of the above embodiments of modules, with bent away apices of geometrical figures or with dents along the periphery, may be provided with additional dents cut out in the body of the head member, thereby increasing the number of needles and/or fastening members.

Each module may be composed of two semimodules with the same shapes and sizes of head members, disposed one above another and fastened together, one semimodule being provided with needles, and the other, with fastening members in the form of triangular dents made integrally with semimodule head members, disposed in the spaced relationship between said head members and bent away therefrom at the right angle in the same direction, at least dents of one semimodule being passed through the applicator base member and through gaps between the dents of the second semimodule and bent away to the surface thereof; the size of gaps between semimodule dents being selected under condition of preservation of base member material between adjacent dents.

Such embodiment of the module provides a more rigid brace between modules and applicator base member. Semimodules are interchangeable, i.e. each semimodule can carry either needles or fastening members, since both semimodules are made with the use of the same technology. Fastening of modules to the applicator base member becomes somewhat more complicated since two semimodules have to be mounted in certain positions with respect to one another.

Here, semimodules may be shaped as two equilateral triangles with rectilinear or concave sides, and with triangular dents in the form of triangle apices bent away from the head member in the same direction and at the right angle, one triangle being turned in its plane with respect to the other triangle by the angle of 60°.

Such embodiment of semimodules ensures a more rigid brace between dents and head members, and hence a more rigid brace between semimodules, which results in a more rigid brace between modules and applicator base member. Angular shift of triangles ensures passage of dents of one module through the gaps between dents of the other module.

Semimodules may be made circular or oval or polygonal, with protruding periphery of head members and triangular dents bent away therefrom.

Such semimodules provide the possibility of increasing the density of needles arrangement and the number of fastening members.

Here, the semimodule with needles may be provided with a central opening and equipped with additional needles shaped as triangular dents protruding from the central opening towards the center of semimodule head member, and bent away from the head member in the same direction as module needles.

Such arrangement results in additional increase in the density of needles arrangement in the applicator.

Each semimodule may be provided with a central opening and a narrow bridge formed between periphery of the head member and said opening, and with triangular dents protruding from the central opening with points thereof directed at the center of the head member and bent away therefrom.

Such embodiment of modules provides a higher density of needles arrangement, and a considerable number of fastening members at comparatively small sizes of modules and small mass thereof.

Here, a semimodule provided with needles may be equipped with additional needles shaped as triangular dents protruding outwards from the head member periphery and bent away in the same direction as module needles.

Such arrangement increases the number of needles on a single module since it results in an increase in their density without increasing module dimensions.

In all the embodiments of modules or semimodules, triangular dents may be made elongated, with curvilinear concave or convex sides.

This makes the needles thinner and sharper.

In all the embodiments of semimodules, their dents may be passed through the applicator base member in opposite directions. This weakens the applicator base member but removes the load from fastening members during applicator use.

Semimodules with needles, except those provided with central openings, may be equipped with additional needles shaped as triangular dents cut out in the head member body at a distance from the periphery thereof, and bent away at the right angle from the head member in the same direction as module needles.

This increases the number of needles without increasing module dimensions.

The number of dents may be ample, thereby causing the possibility of increasing the density of needles arrangement in the applicator and/or increasing the number of fastening members; an increase in the number of dents however causes an increase in the sizes of semimodule head members and hence a decrease in the applicator flexibility.

It is expedient to choose the number of dents that perform the function of needles within the range of one to seven.

It has to be noted that needles may be made as sharpened rods, nails, or pins, fastened in head members of modules or semimodules, and fastening members, as plates fastened in head members of modules or semimodules.

BRIEF DESCRIPTION OF DRAWINGS

The invention is further explained by way of figures, wherein

FIG. 88 demonstrates a fragment of the applicator, view along arrow Y of FIG. 87;

FIG. 89 shows the diagram of mounting semimodules of FIGS. 86, 87 to the applicator base member, top view;

FIG. 90 is the same, side view, section on ZZ;

FIG. 91 is the diagram of arrangement, on the applicator base member, of modules shaped as triangles and provided with dents in the form of bent away triangle apices, and three dents made in the head member body, top view;

PREFERRED EMBODIMENT OF THE INVENTION

Figure 1:
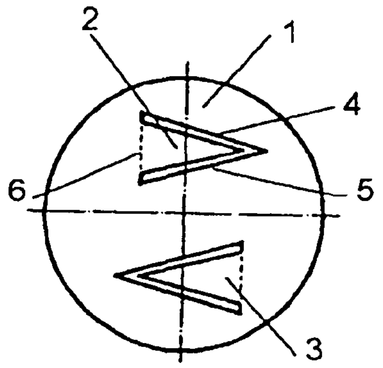
FIG. 1 shows the applicator module with two triangular dents prior to bending the dents from the head member, top view.

The modular applicator comprises a module with head member 1 (FIG. 1) provided with one needle and one fastening member, made in the body of head member 1 integrally with said head member in the form of triangular dents 2 and 3 respectively, and bent away at the right angle from head member 1 in opposite directions (FIGS. 2, 3), dents 2 and 3 being cut in the body of head member 1 along two sides 4 and 5, and bent away at the right angle from head member 1 along the third side, i.e. along base 6 of dent 2 or 3 (FIG. 1). Fastening member, i.e. triangular dent 3, is passed through base member 7 of the applicator (FIG. 3) and bent away (FIG. 4) in pressed relationship to the surface of the applicator base member, which is opposite to the module head member.

Figure 5:
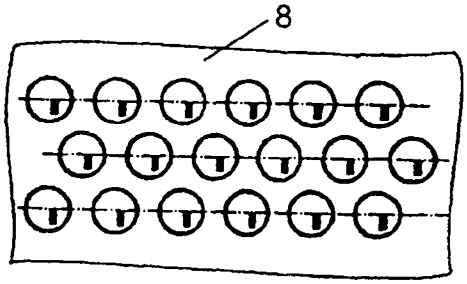
FIG. 5 shows the matrix of modules arrangement, top view.
Figure 6:
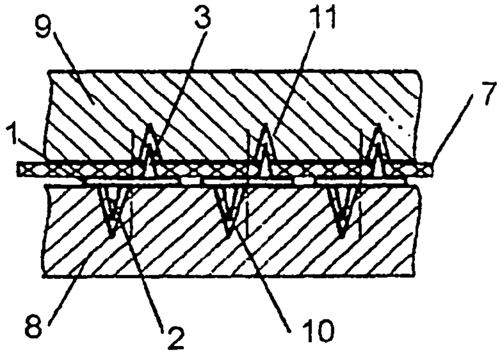
FIG. 6 demonstrates the device for mounting modules in the applicator base member, cross-section.

Modules are made e.g. on blanking and bending dies, using the well-known technology. With the purpose of mounting modules in the applicator base member, two matrices 8 and 9 (FIGS. 5, 6) are used, provided with openings 10 and 11 whose shapes correspond to dents 2 and 3. Openings 10 are disposed in matrix 8 in compliance with the required arrangement of needles (dents 2) in the applicator, and openings 11, in compliance with the arrangement of fastening members (dents 3) on matrix 9. Modules are mounted with their dents 2 into openings 10 of matrix 8; base member 7 is placed on top of said modules, and matrix 9 is placed on top of base member 7 to ensure correspondence between matrix openings 11 and arrangement of dents 3. Matrix 9 is moved under pressure toward matrix 8, due to which fact dents 3, i.e. fastening members, pass through base member 7; following this, matrix 9 is removed, and dents 3 are bent away to the surface of base member 7 and pressed thereto with the use of e.g. roller or roller device (not shown).

Figure 7:
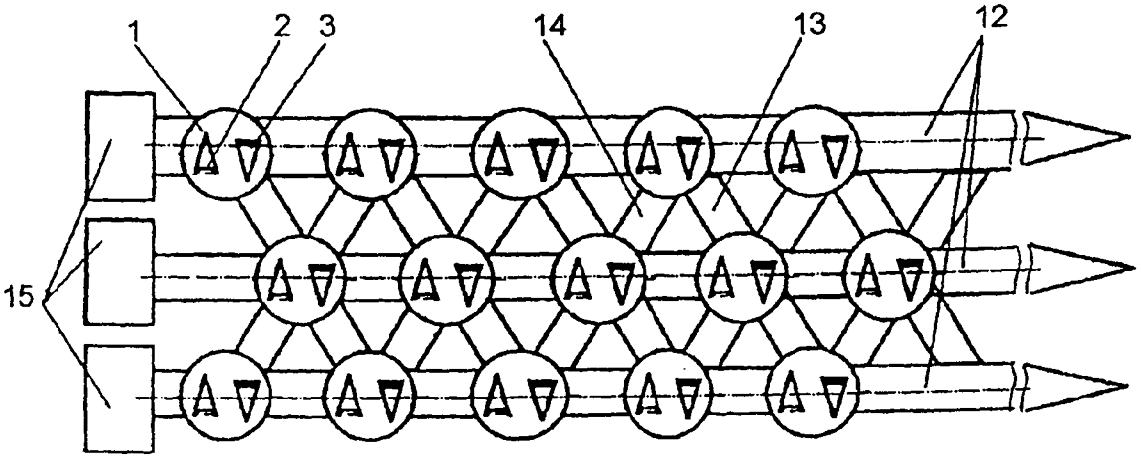
FIG. 7 shows the diagram of the modular applicator with modules, one of which is shown in FIG. 2.

Applicator may be made e.g. with a base member in the form of straps 12 that are connected by means of straps 13 and 14 (FIG. 7). At the intersections of these straps, modules with head members 1 and needles (dents 2) are fixed by means of fastening members (dents 3). Latches or buckles 15 are fastened to one end of each strap 12, and used to fasten opposite ends thereof.

The modular applicator operates as follows.

A required part of the user's body, e.g. shin, forearm, is wrapped by the applicator in such way that the points of needles 2 are directed toward the body surface, and is fixed on this part by way of fixing the ends of straps 12 in latches or buckles 15. Following this, the user is doing exercises that involve long amplitudes of swings, bends, and torsions of individual body members; in so doing, needles 2 act on user's epidermis with unsteady intensity, thereby providing a good reflexotherapeutic effect. When pressing the applicator against the user's body, needles 2 transmit these pressing forces to head members 1 of modules, and the latter transmit these forces with all their surface to applicator base member 7. Thus, fastening members 3 are not loaded by operational forces; these forces only prevent modules from separation from base member 7, and from vibrations of these modules.

This applicator, as can be seen from FIG. 7, features uniform filling of base member 7 with needles 2, and a higher flexibility caused by small sizes of head members 1; it has however low extent of filling of base member 7 with needles 2, and low strength and rigidity of brace between modules and base member 7. In addition, the applicator is characterized by the simplest technology of modules manufacture since both needles (dents 2) and fastening members (dents 3) are made with the use of the same operations (cutting and bending away the dents), and the simplest technology of applicator assembling, since such technology permits the use of rollers or roller device to bend dents 3 away in one run.

It should be noted that base member 7 of the applicator may be made solid, e.g. from a woven material.

Figure 8:
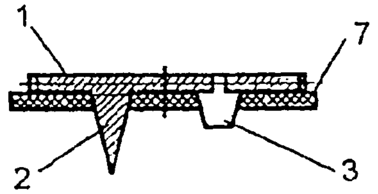
FIG. 8 demonstrates a fragment of the applicator with the module provided with two dents (fastening member and needle) bent away in the same direction, section along needle.

Dents 2 and 3 of the module shown in FIG. 1 may be bent away from head member 1 in the same direction (FIG. 8). Dents 2 and 3 are passed through base member 7 of the applicator, dents 3 (fastening members) being bent away to the surface of base member 7. The operation of bending away dents 2 and 3 in the same direction is simpler then bending them away in opposite direction; it however requires passing both dents 2 and dents 3 through the applicator base member 7, thereby weakening said base member and complicating dents 3 bending away to the surface of base member 7, since bending rollers have to be rolled around dents 2.

Figure 9:
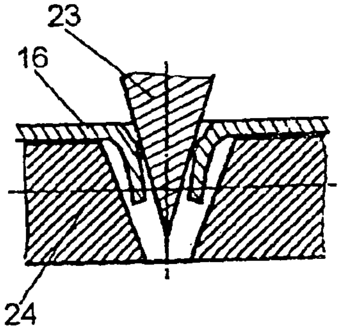
FIG. 9 shows the diagram of making a set of lobes, cross-section.
Figure 10:
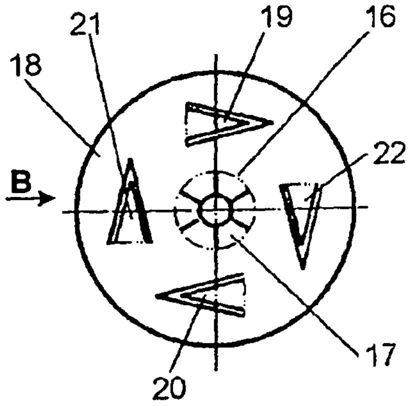
FIG. 10 demonstrates the module provided with four needles and fastening members in the form of a set of lobes, produced by drawing with a conical punch, top view.
Figure 11:
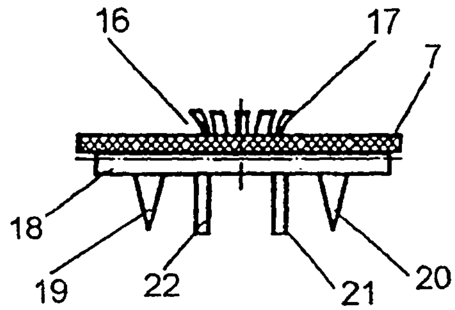
FIG. 11 shows a fragment of the applicator provided with the module of FIG. 9, prior to bending away the lobes, view of the module along arrow B of FIG. 10.
Figure 12:
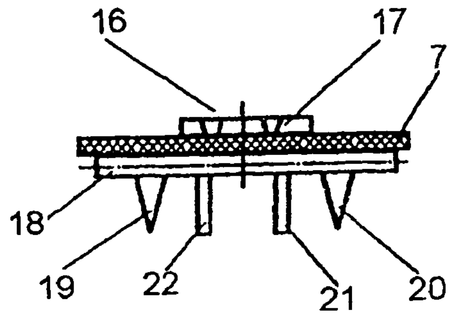
FIG. 12 demonstrates a fragment of the applicator with lobes bent away to its surface.

Fastening member may be made in the form of at least one set 16 of circumferentially disposed lobes 17 (FIGS. 9, 10) made in head member 18 of the module e.g. in the direction which is opposite to dents 19-22 that perform the function of needles. Set 16 of lobes 15 is made (FIG. 9) by drawing with a conical punch 23 and matrix 24; in so doing, set 16 is broken away into separate lobes 17. Lobes 17 are passed through base member 7 of the applicator (FIG. 11) and bent away along circle radii to the surface of base member 7 (FIG. 12). Set 16 of lobes 17 provides a compact arrangement of several fastening members, thereby ensuring a higher strength of brace between the modules and the applicator base member, and leaving a larger area for arrangement of needles, i.e. four dents 19-22; it however complicates the technology of making modules and fastening them to the applicator base member 7.

Figure 13:
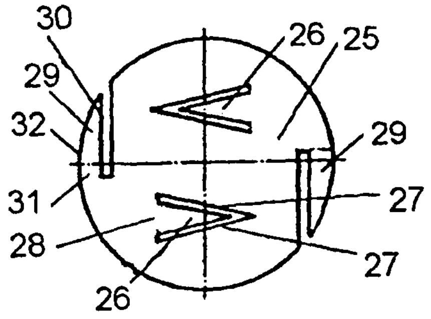
FIG. 13 shows the applicator module provided with two fastening members shaped as dents cut out in the head member body, at a distance from its periphery, and two needles shaped as dents cut out at the periphery of the of the head member, prior to bending dents away, top view.
Figure 14:
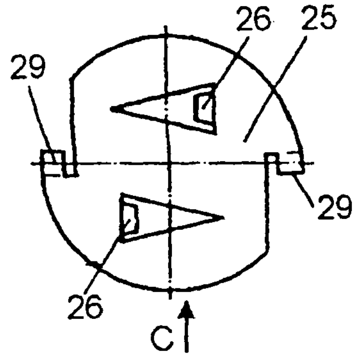
FIG. 14 is the same but after bending dents away.
Figure 15:
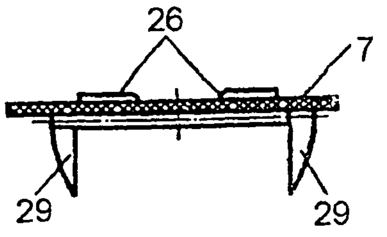
FIG. 15 is a fragment of the applicator, view of the module along arrow C of FIG. 14.

The module (FIGS. 13-15) is provided with head member 25, two fastening members shaped as triangular dents 26 cut out in the body of head member 25 at a distance from its periphery on two sides 27 of dent 26, and bent away at the right angle around the third side 28, and two needles shaped as triangular dents 29 cut out in head member 25 beginning from its periphery along one side 30 of dent 29, and bent away at the right angle along the second side 31, the other side 32 of dent 29 being formed by a section of peripheral edge of head member 25.

Figure 2:
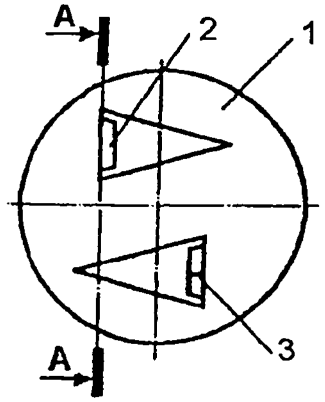
FIG. 2 demonstrates the applicator module upon bending the dents in opposite directions, top view.
Figure 3:
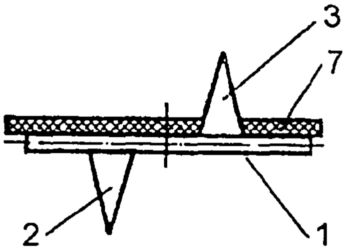
FIG. 3 shows the diagram of module mounting in the base member, side view.
Figure 4:
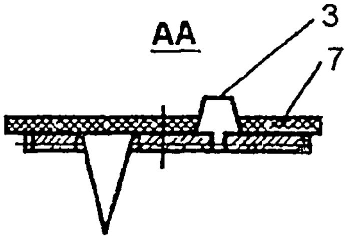
FIG. 4 demonstrates a fragment of the applicator with the module of FIG. 2, section AA.

Manufacture of modules and mounting them to base member 7 are similar to those shown in FIGS. 1-7. Such embodiment of modules ensures a higher strength of brace between modules and applicator base member 7, and a higher density of needles (dents 26) arrangement on base member 7 with the same diameter of head member 25 than in case of using modules with head members 1 (FIGS. 1,2).

Figure 16:
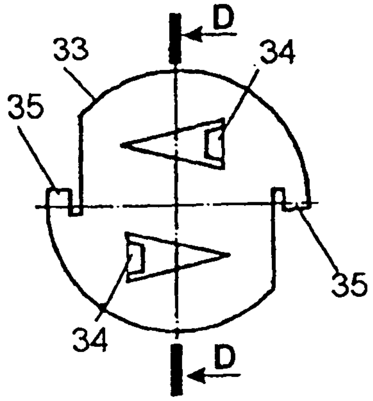
FIG. 16 demonstrates the applicator module provided with two needles shaped as dents cut out in the head member body at a distance from its periphery, and two fastening members shaped as dents cut out at the head member periphery, prior to bending dents away, top view.
Figure 17:
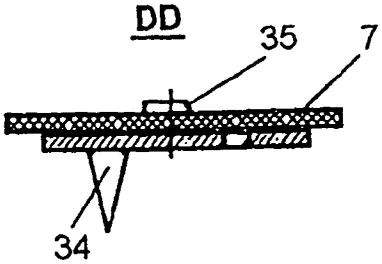
FIG. 17 shows a fragment of the applicator, section DD of the module of FIG. 16.

The module with head member 33 (FIGS. 16, 17) is provided with two needles shaped as triangular dents 34 cut out in the body of head member 33 at a distance from periphery thereof, and two fastening members shaped as triangular dents 35 cut out in head member 33 beginning from its periphery, and bent away from the head member at the right angle. Dents 35 (fastening members) are passed through base member 7 of the applicator, bent away to its surface, and pressed against this surface (FIG. 17). Compared to the previous embodiment, this applicator provides somewhat higher strength and rigidity of brace between head members 33 and base member 7, since dents 35, i.e. fastening members, are disposed at a longer distance from one another.

Figure 18:
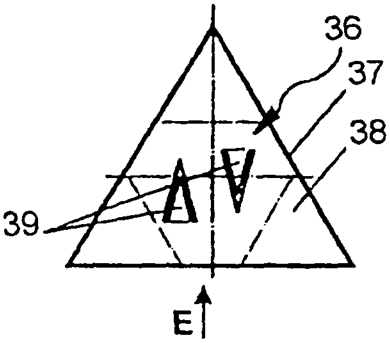
FIG. 18 demonstrates the applicator module shaped as a triangle with rectilinear sides, fastening members in the form of bent away apices of the triangle, and needles shaped as dents cut out in the head member body, prior to bending dents away, top view.
Figure 19:
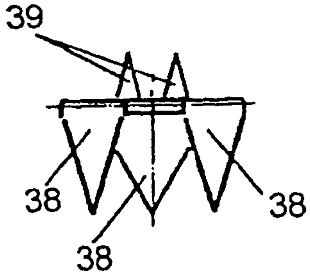
FIG. 19 is the same, after bending dents away, view along arrow E of FIG. 18.
Figure 20:
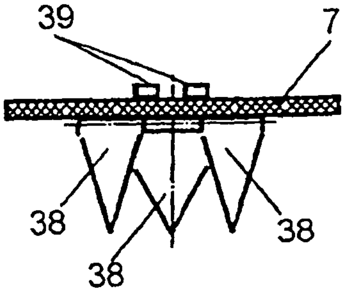
FIG. 20 shows a fragment of the applicator with the module shown in FIGS. 18, 19, view along arrow E of FIG. 18.

Head member 36 of the module is shaped as a triangle with rectilinear sides 37 (FIGS. 18-20), and needles are shaped as triangular dents 38 formed by bending away apices of said triangle at the right angle. Fastening members may be shaped as triangular dents 39 cut out in the body of head member 36 and bent away therefrom at the right angle and in the direction opposite to dents 38. Dents 39 are passed through base member 7 of the applicator, bent away to its surface, and pressed against this surface (FIG. 20). Technology of manufacturing these modules is somewhat different from that shown in FIGS. 5,6, since dents 38 instead of being cut out in the body of head member 36 are only bent away. The above embodiment of dents 38 ensures their stronger brace with head member 36.

Figure 21:
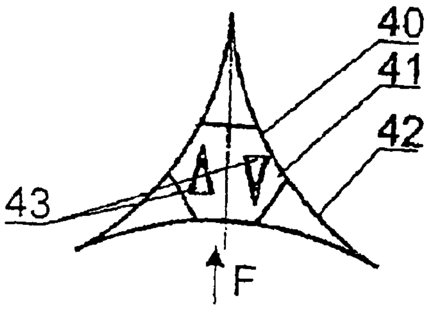
FIG. 21 demonstrates the applicator module shaped as a triangle with concave sides, with needles shaped as bent away triangle apices, and fastening members shaped as dents cut away in the head member body, prior to bending dents away, top view.
Figure 22:
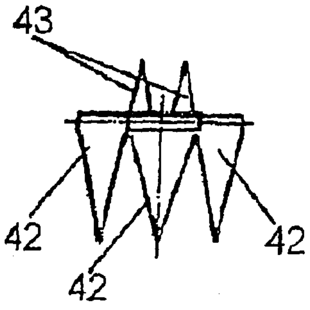
FIG. 22 is the same, but after bending dents away, view along arrow F of FIG. 21.
Figure 23:
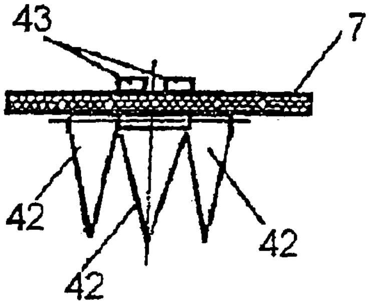
FIG. 23 shows a fragment of the applicator with the module of FIGS. 21, 22, view along arrow F of FIG. 18.

The module having head member 40 is shaped as a triangle with curvilinear concave sides 41 (FIG. 21), and needles are shaped as triangular dents 42 formed by triangle apices bent away at the right angle (FIG. 22). Fastening members are shaped as triangular dents 43 cut out in the body of head member 40 and bent away therefrom at the right angle. Dents 43 are passed through base member 7, bent away to its surface, and pressed against this surface (FIG. 23). Such embodiment of the module ensures a better sharpness of dents 42 (needles).

Figure 24:
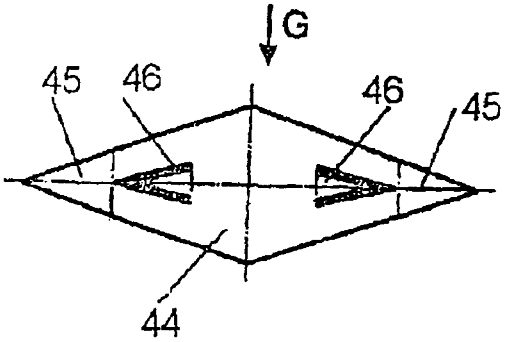
FIG. 24 demonstrates the applicator module shaped as rhomb with needles in the form of two of its acute-angled bent away apices, and fastening members shaped as dents cut out in the head member body, prior to bending dents away, top view.
Figure 25:
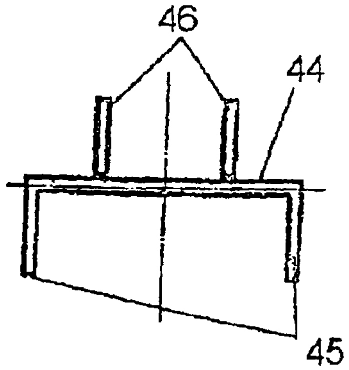
FIG. 25 is the same, after bending dents away, view along arrow G of FIG. 24.
Figure 26:
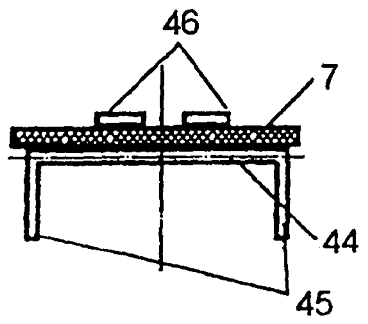
FIG. 26 shows a fragment of the applicator with the module of FIGS. 24, 25, module view along arrow G of FIG. 24.

The module having head member 44 is shaped as a rhomb (FIG. 24), and needles or fastening members are shaped as triangular dents 45 formed by its two acute-angled apices bent away at the right angle (FIG. 25). Dents 46 are performing e.g. the function of needles, while the function of fastening members is performed e.g. by two triangular dents 46 cut out in the body of head member 44 and bent away therefrom at the right angle. Dents 46 are passed through applicator base member 7, bent away to its surface, and pressed against this surface (FIG. 26). From the standpoint of its properties and production technology, the module having head member 44 is similar to the module with head member 40.

Figure 27:
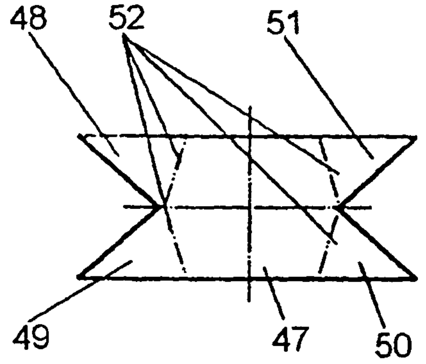
FIG. 27 is the applicator module shaped as a rectangular and with two dents on its opposite sides, prior to bending dents away, top view.
Figure 28:
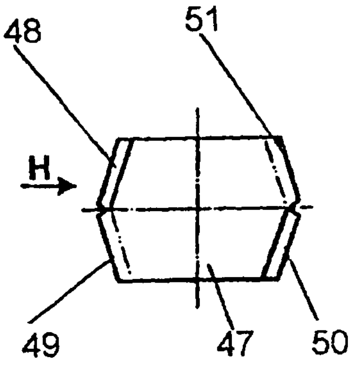
FIG. 28 is the same, after bending dents away, top view.
Figure 29:
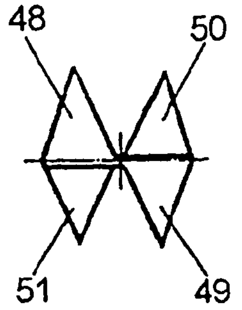
FIG. 29 is the same, after bending dents away, view along arrow H of FIG. 28.

The module having head member 47 is shaped as a rectangle (FIGS. 27 through 29), and needles and fastening members are shaped as triangular dents 48 through 51 formed by triangular beams protruding from two opposite sides of the rectangle, their bases 52 being disposed on these sides close to one another, and points of dents are directed outwards from head member 47, two dents 48 and 50 disposed on the same diagonal being bent away along bend lines 52 to one side, and two dents 49, 51 disposed on the other diagonal being bent away to the other side (FIGS. 28, 29). If all dents 48 through 51 were bent away in the same direction, then in the course of passing all them through base member 7 of the applicator they would cut said base member in locations of dents 48 through 51; in addition, it would be necessary to provide additional dents that would perform the function of fastening members, e.g. in the form of dents cut out at a distance from periphery of head member 47.

Figure 30:
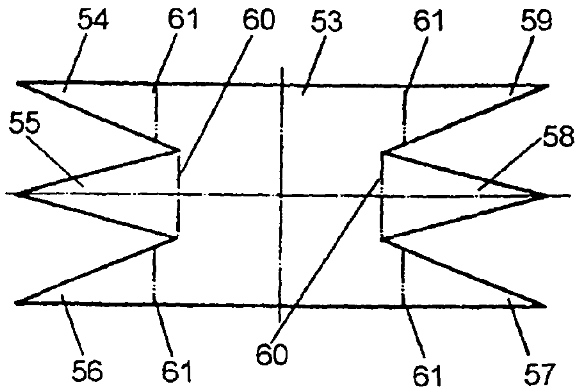
FIG. 30 is the applicator module shaped as a rectangle provided with three dents on its opposite sides, prior to bending dents away, top view.
Figure 31:
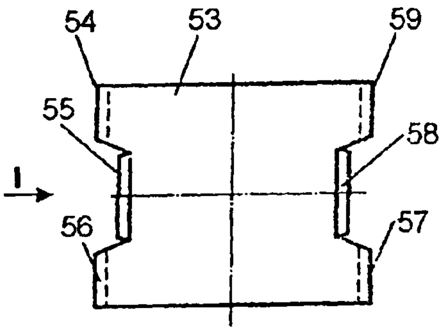
FIG. 31 is the same, after bending dents away, top view.
Figure 32:
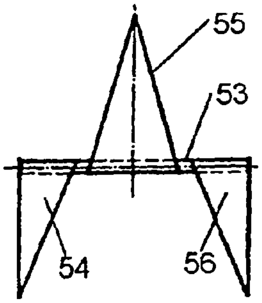
FIG. 32 is the same, after bending dents away, view along arrow I of FIG. 31.
Figure 33:
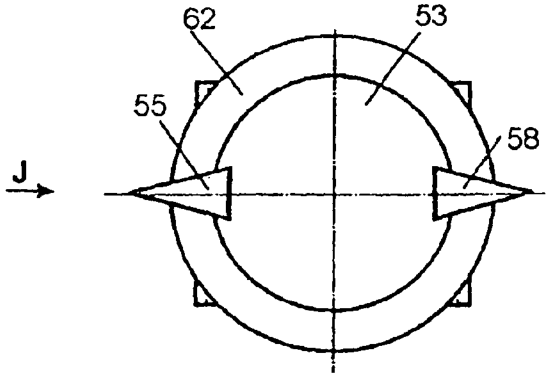
FIG. 33 demonstrates the applicator with the module shown in FIGS. 31-32, with a washer disposed between the bent away dents and applicator base member, view along arrow I of FIG. 31.
Figure 34:
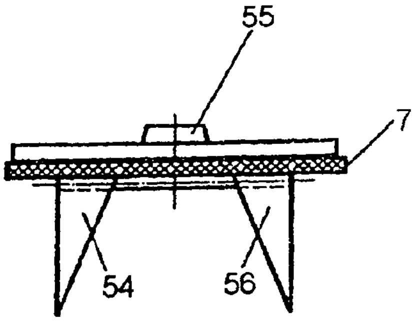
FIG. 34 is the same, view along arrow J of FIG. 33.

Each side of rectangular head member 53 (FIGS. 30 through 32) may be provided with three dents 54 through 59, central dents 55 and 58 being bent away to one side along bend lines 60, and extreme dents 54, 56, 57, and 59, along bend lines 61 to the other side. Central dents 55 and 58 (fastening members) (FIGS. 33, 34) are passed through base member 7 of the applicator and an opening in washer 62, bent away to the surface of washer 62, and pressed against this surface. Dents 54, 56, 57, and 59 perform the function of needles.

Applicators with the above modules operate similarly to applicators with the modules shown in FIGS. 1 through 4, 7.

Figure 35:
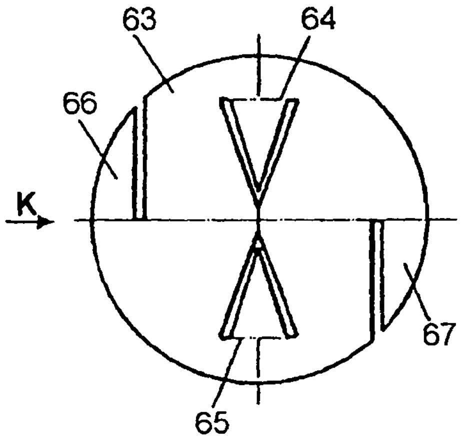
FIG. 35 shows the applicator module with two dents spaced from head member periphery, and two dents on head member periphery, top view.
Figure 36:
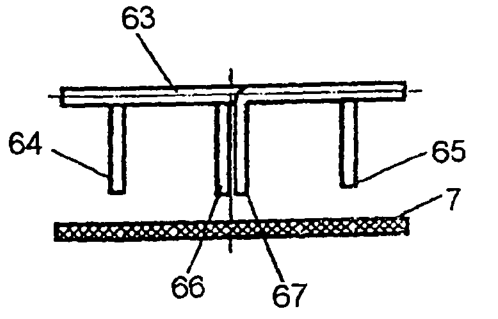
FIG. 36 is the same, with dents bent away in the same direction, view along arrow K of FIG. 35.
Figure 37:
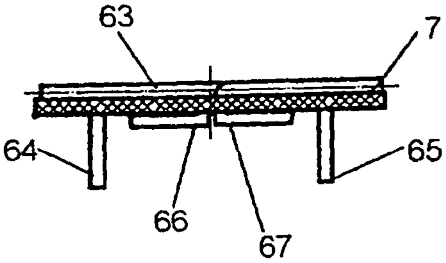
FIG. 37 demonstrates a fragment of the applicator, view along arrow K of FIG. 35.

The module having head member 63 (FIG. 35) is provided with four dents 64 through 67, bent away to one side (FIG. 36). All dents 64 through 67 are passed through base member 7 of the applicator (FIG. 37), dents 66 and 67 that perform the function of fastening members being bent away to the surface of base member 7 of the applicator, and dents 64 and 65 performing the function of needles.

The applicator with the above modules operates as follows.

Needles 64, 65 transfer transmit forces generated by pressure of the applicator against user's body to head members 63 of the modules, and the latter transmit these forces to fastening members 66, 67, thereby loading them with bending moments, which fact causes insufficient reliability and durability of modules.

Figure 38:
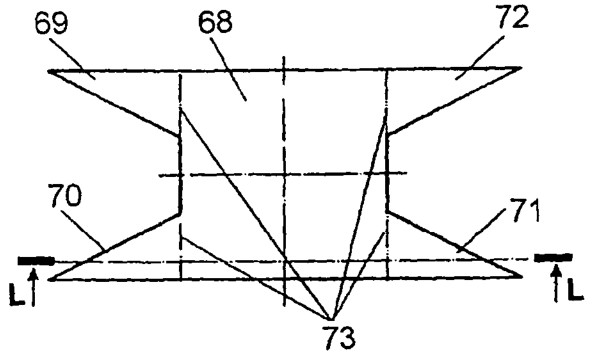
FIG. 38 shows the applicator module with a head member shaped as rectangle with two dents on its opposite sides, top view.
Figure 39:
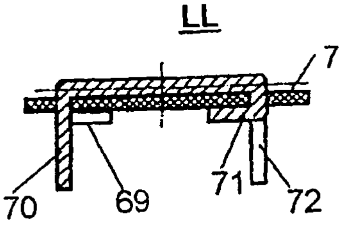
FIG. 39 demonstrates a fragment of the applicator with the module of FIG. 38, section on LL of FIG. 38.

Head member 68 (FIG. 38) is provided with four dents 69 through 72, bent away to one side, dents 69 and 70, as well as dents 71 and 72 being disposed with gaps between their bases 73. All dents 69 through 72 are passed through base member 7 of the applicator, dents 70 and 72 (needles) remaining non-bent, and dents 69 and 71 (fastening members) being bent away to the surface of applicator base member 7 (FIG. 39).

Figure 40:
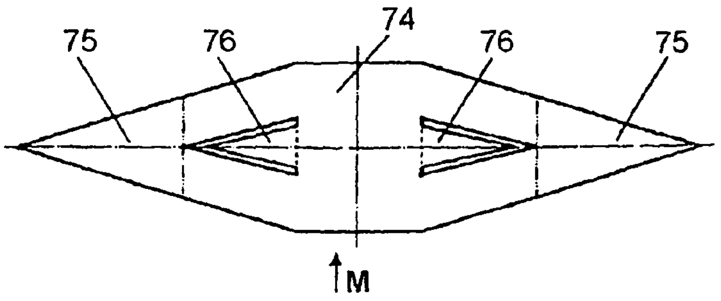
FIG. 40 shows the applicator module with a head member shaped as hexagon with two dents in the form of its two bent away acute-angled apices, and two dents spaced from its periphery, top view.
Figure 41:
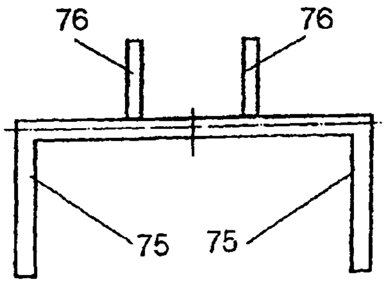
FIG. 41 is the same, with bent away dents, view along arrow M of FIG. 40.
Figure 42:
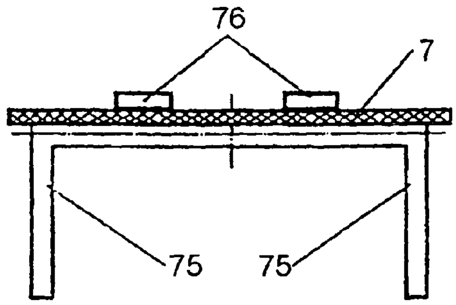
FIG. 42 demonstrates a fragment of the applicator with the module of FIGS. 40 and 41, view along arrow M of FIG. 40.
Figure 43:
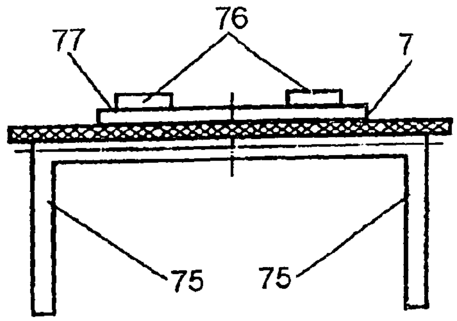
FIG. 43 is the same, with the washer disposed between bent away fastening members and the surface of the applicator base member.

The module having head member 74 is shaped as a rhomb (FIGS. 40, 41), and needles are shaped as triangular dents 75 formed by its two acute-angle apices bent away at the right angle. The function of fastening members is performed by two triangular dents 76 cut out in the body of head member 74 and bent away therefrom at the right angle in the direction opposite to dents 75. Dents 76 are passed through base member 7, bent away to its surface and pressed against this surface (FIG. 42). Washer 77 (FIG. 43) may be mounted between dents 76 and applicator base member 7.

Figure 44:
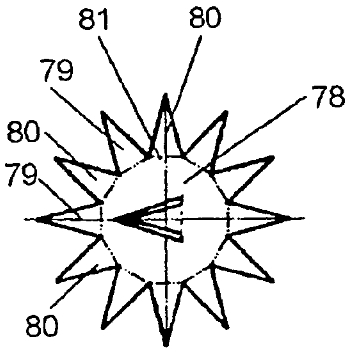
FIG. 44 is the applicator module with a circular head member, dents disposed along its periphery, and one dent disposed in the head member center, top view.
Figure 45:
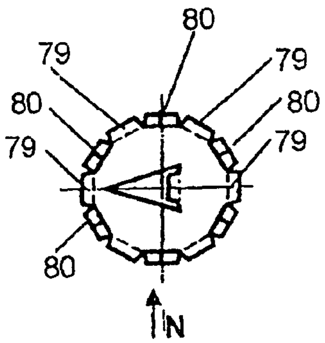
FIG. 45 is the same, with bent away dents.
Figure 46:
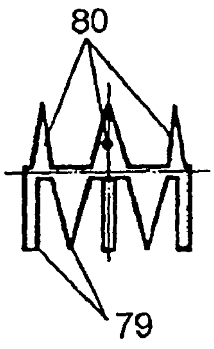
FIG. 46 is the same, view along arrow N of FIG. 45.
Figure 47:
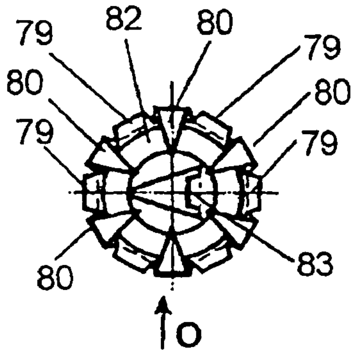
FIG. 47 demonstrates a fragment of the applicator with the module of FIGS. 44 through 46, and with the washer disposed between bent away dents and the applicator base member, said base member being conditionally displaced, top view.
Figure 48:
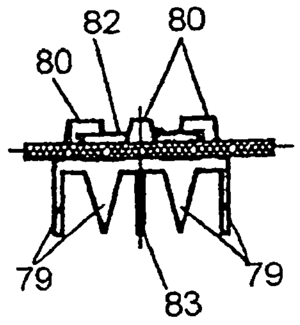
FIG. 48 is the same, view along arrow O of FIG. 47.

The module having head member 78 (FIG. 44) is shaped as a circle, and needles and fastening members, as triangular dents 79, 80 formed by beams protruding from the periphery of head member 78, their bases 81 being closely disposed along this periphery. Dents 79, 80 are bent away from head member 78 alternatively in opposite directions. Dents 80 (fastening members) are bent away to the surface of base member 7 of the applicator (FIGS. 47, 48), and dents 79 (needles) remain non-bent, washer 82 being mounted between dents 80 and base member 7. One more dent 83 (needle) is cut out in head member 78.

Figure 49:
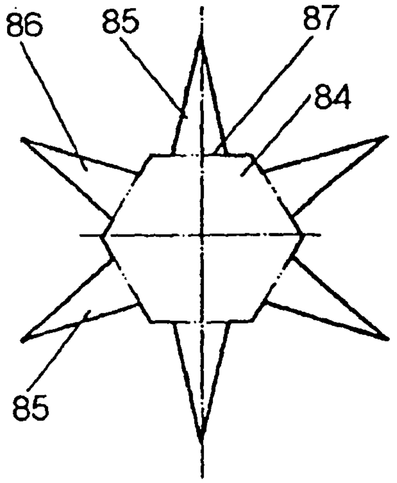
FIG. 49 shows the applicator modules shaped as hexagon with triangular dents whose bases are disposed in central members of hexagon sides, top view.
Figure 50:
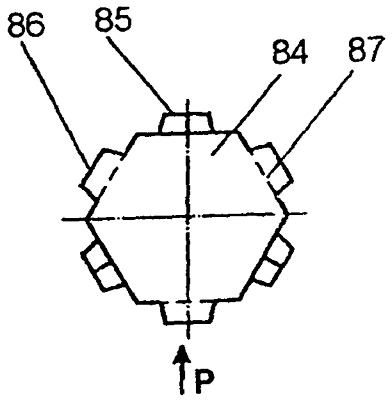
FIG. 50 is the same, with bent away dents, top view.
Figure 51:
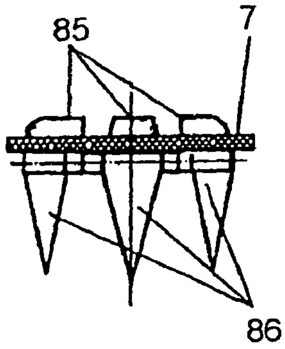
FIG. 51 is a fragment of the applicator, view along arrow P of FIG. 50.

The module having head member 84 is shaped as a regular polygon (FIG. 49), and needles and fastening members, as triangular dents 85, 86 formed by beams protruding from the sides of head member 84, their bases 87 being disposed along central sections of these sides. Dents 85, 86 are bent away from head member 84 alternatively in opposite directions (FIG. 50). Dents 85 (fastening members) are passed through base member 7 of the applicator, bent away to its surface and pressed against this surface (FIG. 51), while dents 86 (needles) remain non-bent.

Figure 52:
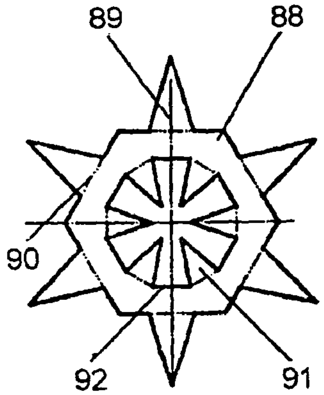
FIG. 52 demonstrates the applicator module shaped as hexagon with triangular dents whose bases are disposed in central members of hexagon sides, and dents disposed along periphery of the central opening provided in the head member, top view.
Figure 53:
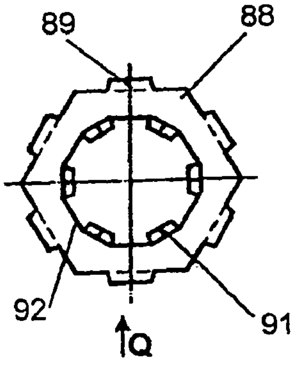
FIG. 53 is the same, with bent away dents.
Figure 54:
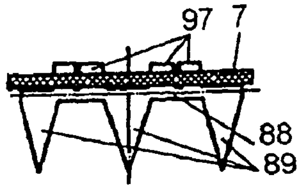
FIG. 54 is the view along arrow Q of FIG. 53.

The module having head member 88 and shaped as a regular polygon (FIG. 52), may be also provided, in addition to dents 89 disposed along central members 90 of any sides of the polygon, with dents 91 formed by beams protruding from central circle 92 with points thereof toward the center of head member 88. Dents 91 that perform the function of fastening members are bent away from head member 88 in the same direction (FIG. 53), while dents 89 that perform the function of needles are bent away in the opposite direction. Dents 91 (fastening members) are passed through base member 7 of the applicator (FIG. 54), bent away to its surface and pressed against this surface (FIG. 54), while dents 89 (needles) remain non-bent.

Figure 55:
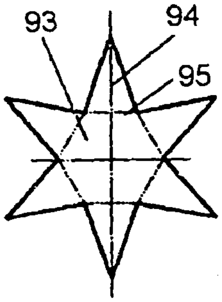
FIGS. 55 through 57 show applicator modules shaped as six-pointed stars, top view.
Figure 56:
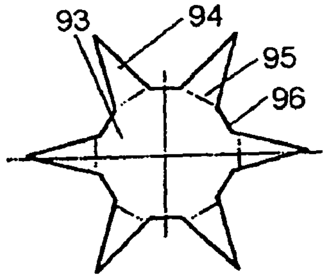
Figure 57:
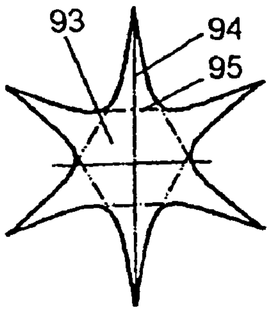
Figure 58:
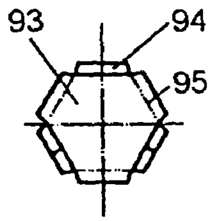
FIG. 58 is the same, with dents in the form of bent away end portions of star beams, top view.
Figure 59:
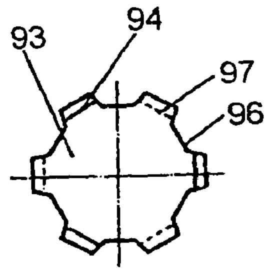
FIG. 59 is the same, with dents in the form of bent away end portions of beams, top view.

The module having head member 93 is shaped as a star (FIGS. 55 through 57), e.g. with six beams 94 disposed with their bases 95 either in close relationship (FIG. 55) or with gaps 96 provided therebetween (FIGS. 56, 57), and needles and fastening members are shaped as triangular dents formed by these beams which are bent away from head member 93 at the right angle alternatively in opposite directions (FIG. 58). Triangular dents may be also bent away (FIG. 59) with end portions thereof along bend lines 97. Mounting of these modules to the applicator base member is similar to the above-described.

Each of the above modules may be equipped with additional needles in the form of triangular dents cut out in the body of head member at a distance from its periphery.

Applicators with the above modules operate similarly to those with the modules shown in FIGS. 1 through 4, and 7.

Figure 60:
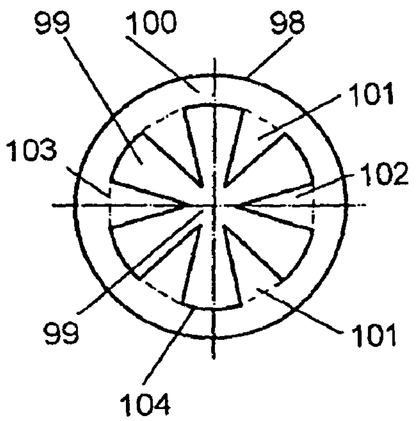
FIG. 60 shows the applicator module shaped as a circle with a central circular opening, and with dents provided along periphery of said circle, top view.
Figure 61:
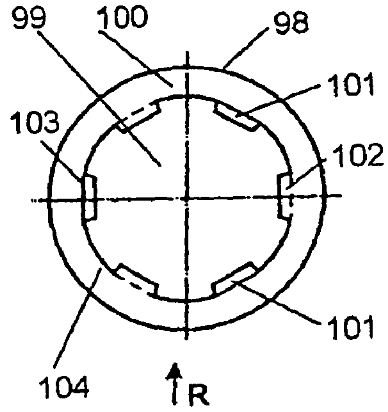
FIG. 61 is the same, with dents bent away in opposite directions, top view.
Figure 62:
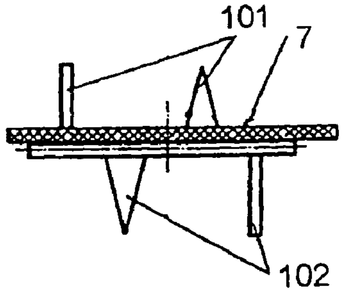
FIG. 62 is a fragment of the applicator, view along arrow R of FIG. 61.
Figure 63:
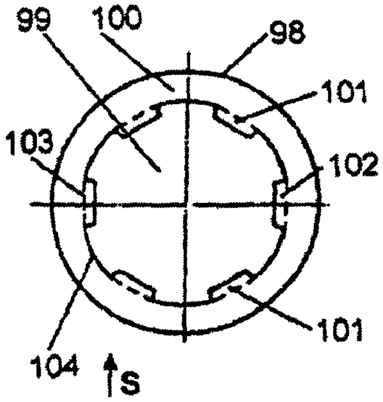
FIG. 63 demonstrates the module of FIG. 60, with dents bent away in the same direction.
Figure 64:
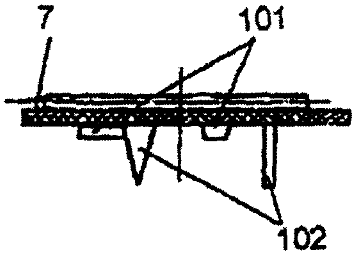
FIG. 64 shows a fragment of the applicator, view along arrow S of FIG. 63.
Figure 65:
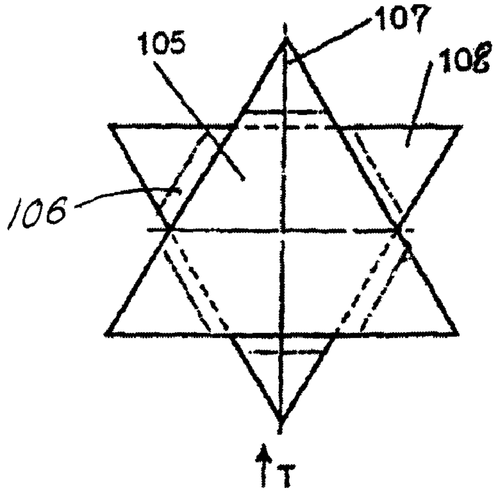
FIG. 65 demonstrates semimodules shaped as triangles, top view.

The module having head member 98 is shaped as a circle (FIG. 60) provided with central circular opening 99 and narrow bridge 100 formed between periphery of head member 98 and said opening, triangular dents 101 and 102 with dent bases 103 disposed along perimeter of the opening with gaps 104 therebetween protruding along perimeter of the opening toward the center of head member 98. Dents 101 and 102 are bent away (FIG. 61) from head member 98 at the right angle in opposite directions. Dents 101 (fastening members) are passed through base member 7 of the applicator (FIG. 62) and bent away to its surface. Dents 101 and 102 may be also bent away in the same direction (FIG. 63) and passed through base member 7 of the applicator, dents 101 (fastening members) being bent away to the surface of base member 7 from the side where dents 102 (needles) are disposed (FIG. 64).

Such embodiment of modules ensures a higher density of needles arrangement and a considerable number of fastening members at comparatively small sizes of modules and small mass thereof.

Applicator with modules shown in FIGS. 63, 64 operates as follows.

Due to the availability of gaps 103 between dents 101 and 102, needles 102 and fastening members 101, despite being bent away in the same direction and passed through base member 7 of the applicator, do not cut completely base member 7 due to the availability of gaps 104 therebetween. Needles 102 transmit forces generated by pressure of the applicator against user's body to head members 98 of modules, and the latter transmit these forces to fastening members 101, thereby loading them with bending moments, which fact causes insufficient reliability and durability of modules.

Figure 66:
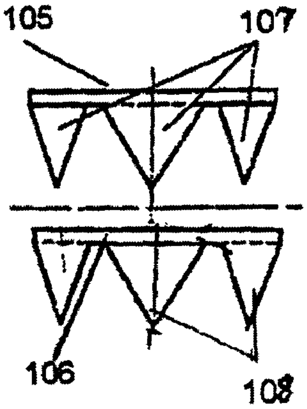
FIG. 66 is the diagram of mounting semimodules of FIG. 65 to the applicator base member, view along arrow T of FIG. 65.
Figure 67:
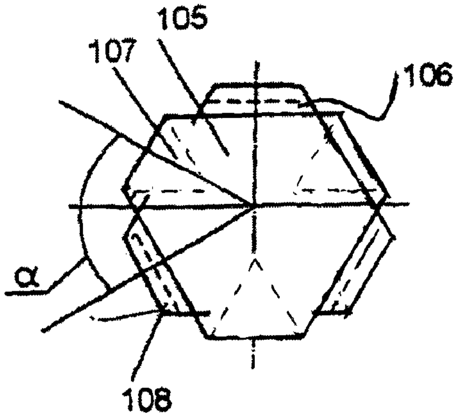
FIG. 67 shows a fragment of the applicator provided with triangular semimodules.
Figure 68:
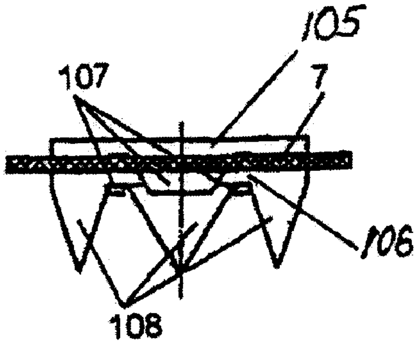
FIG. 68 demonstrates a fragment of the applicator with one semimodule passed through its base member, side view.

With reference to the embodiment shown in FIGS. 65-68, each module may be composed of two semimodules with the same shape and size of head members 105 and 106, disposed one above the other on opposite surfaces of base member 7 of the applicator. These semimodules are shaped as triangles with apices bent away at right angles from head members 105 and 106 in the same direction (FIG. 66). These triangles form triangular dents 107 and 108 (fastening members and needles, respectively). One triangle (head member 106) is turned in its plane with respect to the other triangle (head member 105) by an angle of 60° (see angle α in FIG. 67). Only dents 107 are passed through base member 7 of the applicator, and are then bent parallel to the surface of head member 105. Dents 108 of head member 106 are not bent and perform the function of needles (FIGS. 67 and 68).

The above embodiment of the modular applicator provides a more rigid brace between modules and base member 7 of the applicator. Semimodules are interchangeable, i.e. each semimodule can carry either needles or fastening members, since both semimodules are made with the use of the same technology, i.e. manufacture of modules does not differ from their manufacture for applicators made in compliance with the first embodiment shown in FIGS. 1 through 4 and FIGS. 8 through 82. Fastening of modules to base member 7 of the applicator is somewhat more complicated since two semimodules have to be mounted in certain positions with respect to one another.

The applicator with the above modules operates as follows.

Semimodules with head members 105 and 106 are arranged on opposite surfaces of base member 7 of the applicator (FIGS. 65, 66) in such a way that one triangle (head member 106) is turned in its plane with respect to the other triangle (head member 105) by an angle of 60°. Fastening members 107 of head member 105 are passed through base member 7, following which the fastening members 107 are bent parallel to the major surfaces of head member 105. When pressing the applicator against the user's body, the needles 108 transmit these pressing forces to head member 106 of the semimodules, and the head member 106 in turn transmits these forces with all its surface to base member 7 of the applicator. Thus, fastening members 107 are not loaded by operational forces; they only prevent the semimodules from separating from base member 7, and prevent vibrations of these modules.

Only dents 107 of head member 105 (FIG. 68) can be passed through base member 7 of the applicator. Their points are directed in the same direction as dents 108 of head member 106 (FIG. 66), and are then bent parallel to the surface of head member 105.

Figure 69:
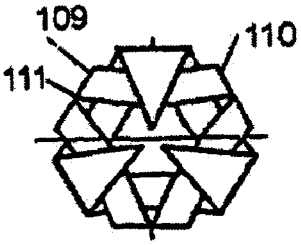
FIG. 69 shows a fragment of the applicator with semimodules shaped as triangles with concave sides and central openings, top view.

Head members 109 and 110 of semimodules may be shaped as triangles with curvilinear concave sides (FIG. 69) and central openings 11 and 112, thereby making the dents that perform the function of needles sharper.

Shaping semimodules as triangles provides a more rigid brace between dents and bodies of head members due to availability of a more rigid brace between semimodules, and hence a more rigid brace between modules and applicator base member.

Figure 70:
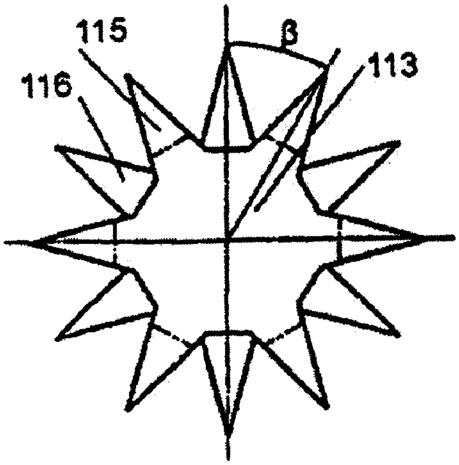
FIG. 70 demonstrates semimodules shaped as stars, top view.
Figure 71:
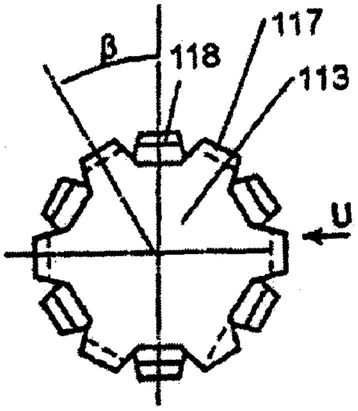
FIG. 71 is the same, with bent away dents, top view.
Figure 72:
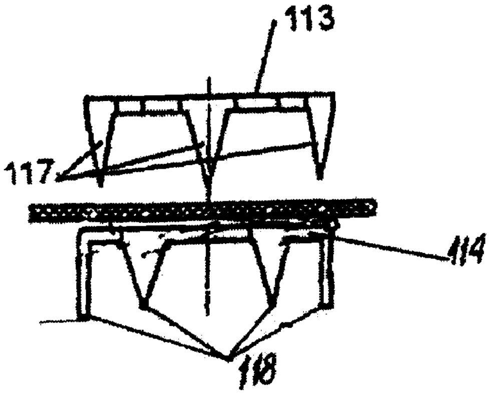
FIG. 72 is the diagram of mounting semimodules of FIGS. 70, 71 to the applicator base member, view along arrow U of FIG. 71.
Figure 73:
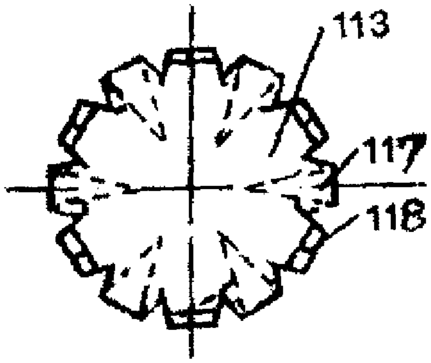
FIG. 73 shows a fragment of the applicator with mounted semimodules of FIGS. 70, 71, top view.
Figure 74:
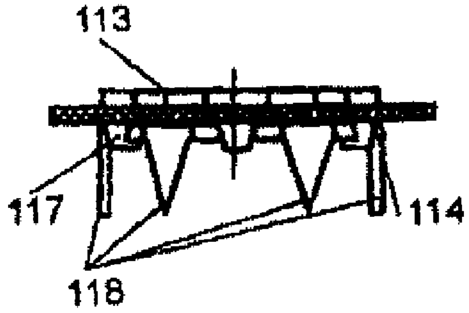
FIG. 74 shows a fragment of the applicator with mounted semimodules of FIGS. 70, 71, and with passing one semimodule through the base member, side view.

Head members 113 and 114 of semimodules may be made as two similarly shaped and sized stars one of which is provided with beams 115, and the other, with beams 116 (FIG. 70). Ends of beams 115 are bent away at the right angle in the same direction, thereby forming triangular dents 117, and ends of beams 116 are also bent way in the same direction, with formation of triangular dents 118 (FIG. 71), head member 113 being turned in its plane relative to head member 114 by an angle of 180°/n, where n is the number of beams of one star, i .e. in the given case by an angle of 30°. Dents 117 and 118 are passed through base member 7 of the applicator in opposite directions (FIG. 72), dents 118 being passed through gaps between dents 117 (and dents 117, through gaps between dents 118) and bent away to the surface of head member 113 (FIG. 73) dents 117 may be passed through base member 7 of the applicator in the direction of location of points of dents 118 and bent away to the surface of head member 114 (FIG. 74). Such embodiment of modules provides the possibility of increasing the density of needles arrangement and the number of fastening members.

Figure 75:
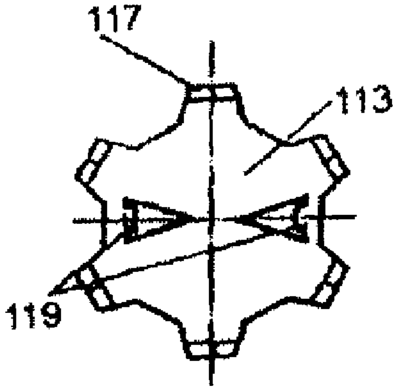
FIG. 75 demonstrates a semimodule shaped as a star, and with additional needles provided in the head member body, top view.
Figure 76:
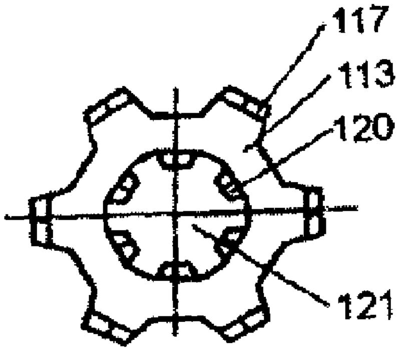
FIG. 76 shows the semimodule shaped as a star and provided with additional needles made around the central opening in the head member, top view.

One of the semimodules in which dents perform the function of needles, e .g. semimodule with head member 114 in FIG. 74, may be equipped with two additional needles shaped as triangular dents 119 cut out in the body of head member 113 at a distance from its periphery, and bent away at the right angle from head member 113 (FIG. 75), or with six needles shaped as triangular dents 120, made within circular opening 121 of head member 113 (FIG. 76), thereby additionally increasing the density of needles arrangement and the number of fastening members.

Figure 77:
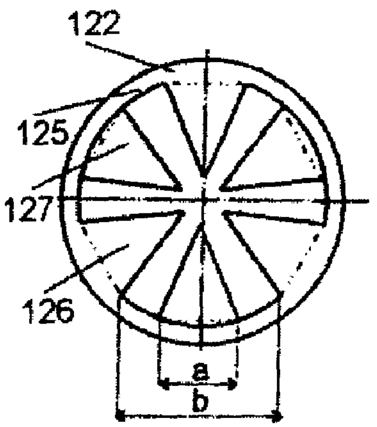
FIG. 77 demonstrates semimodules shaped as circles with central openings, and dents made around these openings, top view.
Figure 78:
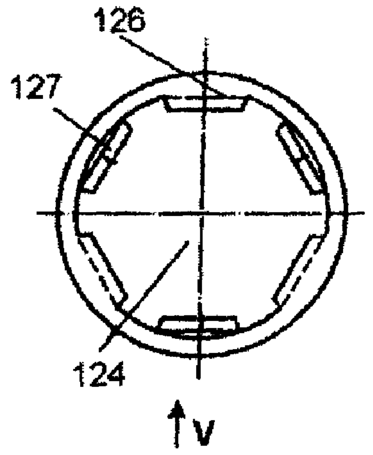
FIG. 78 is the same, with bent away dents, top view.
Figure 79:
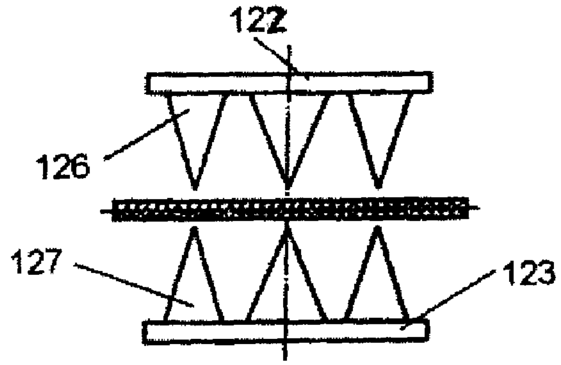
FIG. 79 is the diagram of mounting semimodules of FIG. 78 to the applicator base member, view along arrow V of FIG. 78.
Figure 80:
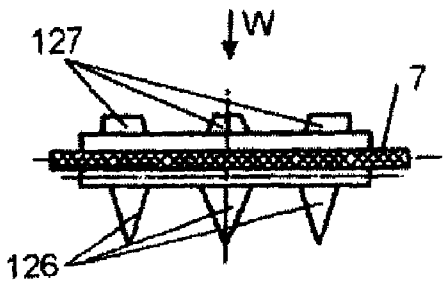
FIG. 80 is a fragment of the applicator with semimodules of FIG. 79, side view.
Figure 81:
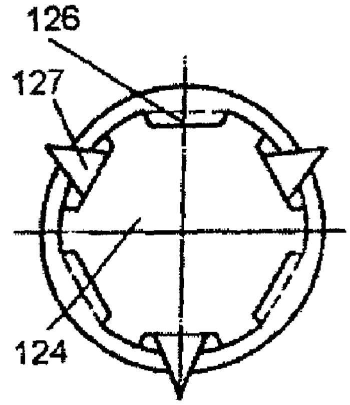
FIG. 81 is the view in the direction of arrow W of FIG. 80.

Each module may be composed of two semimodules with the same shapes and sizes of head members 122 and 123 (FIG. 77), disposed one above another on opposite surfaces of base member 7 of the applicator, each of said head members being provided with circular opening 124 that is concentric with head member periphery, with formation of narrow bridge 125 between head member periphery and opening 124; perimeter of each central opening 124 in head members 122 and 123 is provided with three triangular dents 126 and 127 respectively, protruding toward centers of head members 122 and 123, bases of these dents being disposed along opening perimeter with gaps b whose width exceeds the width a of gaps . Dents 126 and 127 are bent away from head members 122 and 123 at right angles (FIG. 78, passed in opposite directions through base member 7 of the applicator and through gaps b between debt bases a 127 and 126, respectively, dents 127 being bent away to the surface of head member 122 and pressed against this surface (FIGS. 79 through 81) Head member 122 is turned in its plane relative to head member 123 by an angle of 180°/n, where n is the number of dents of each circle, i.e. in the given case by an angle of 60°.

Figure 82:
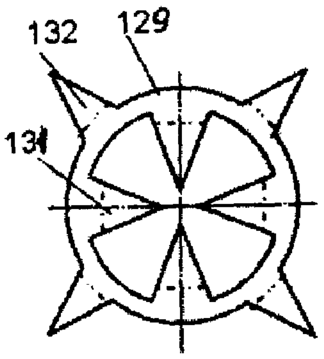
FIG. 82 shows the semimodule shaped as a circle with dents made inside the circle and additional dents around the periphery of the circle, top view.
Figure 83:
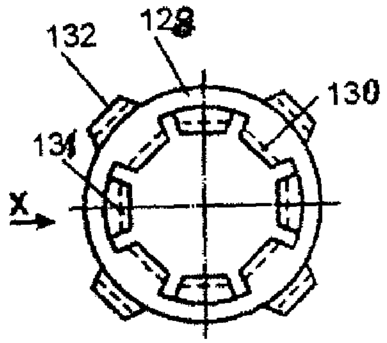
FIG. 83 shows fastening the semimodule to the main semimodule (FIG. 82), top view.
Figure 84:
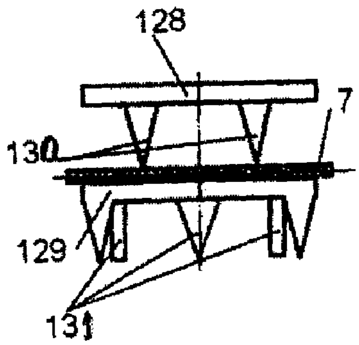
FIG. 84 shows mounting of the semimodules (FIGS. 82, 83) to the base member, side view.
Figure 85:
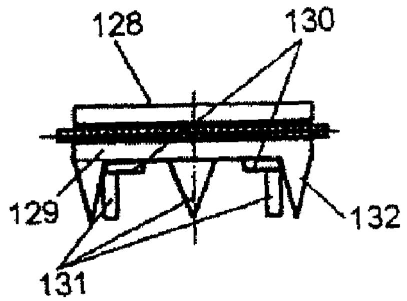
FIG. 85 demonstrates a module that consists of two semimodules (FIGS. 82, 83) and fixed at the base member, side view.

Fastening member 128 and base member 129 are provided with dents 130 and 131, respectively (FIGS. 82, 83). Dents 130 of head member 128 are passed through base member 7 (FIGS. 84, 85) and through gaps between dents 131 of head member 129. Dents 130 of the member 128 are bent away to the surface of member 129 (FIG. 85). Head member 129 may be provided with dents 132.

Figure 86:
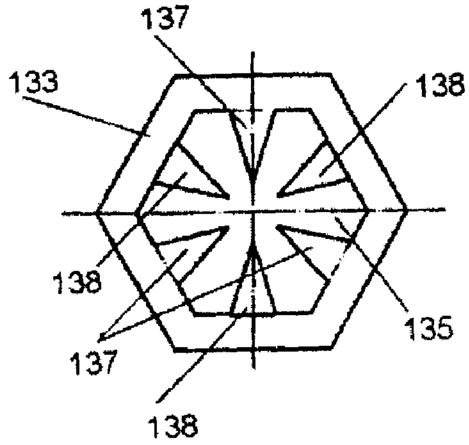
FIG. 86 shows semimodules shaped as hexagons provided with central hexagonal openings, and dents made around said openings, top view.
Figure 87:
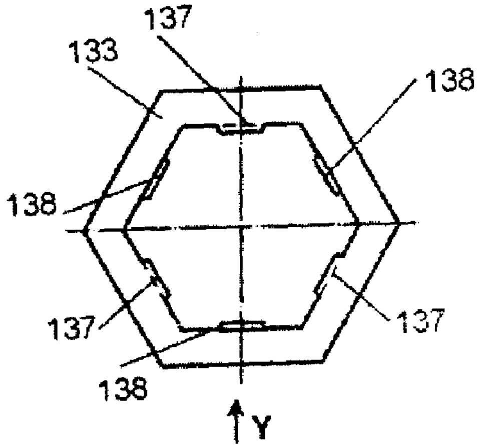

Head members 133, 134 (FIG. 86) of semimodules may be made as two similarly shaped and sized hexagons with hexagonal openings 135, 136 provided with triangular dents 137 and 138 respectively, bent away from head members 133, 134 at the right angle (FIG. 87). Dents 137 (fastening members) of head member 133 are passed through base member 7 of the applicator (FIG. 88) and bent away to the surface of head member 134 whose functions 138 perform the function of needles Embodiments of modules shown in FIGS. 76 through 88 provide a higher density of needles arrangement and a considerable number of fastening members at comparatively small sizes of modules and small mass thereof.

Semimodules shown in FIGS. 65 through 88 are made similarly to the above modules, i.e. by cutting out head members, cutting out and bending away dents, or by cutting out head members and bending awaydents. Fastening of modules composed of two semimodules, e.g. modules shown in FIGS. 86 through 88, is carried out with the use of two matrices one of which, 139, is shown in FIGS. 89 and 90. Matrices 139 are provided with openings 140 in compliance with shapes and sizes of head members 133 of semimodules. Openings 140 are disposed in matrices 139 in compliance with preset arrangement of modules on base member 7 of the applicator. The second matrix (not shown) is made similar to matrix 139. Head members 134 of semimodules are mounted in the second matrix. Head members 133 are mounted into openings 139, with dent points 137 directed upwards; base member 7 of the applicator is laid on dent points 137, and base member edges are fixed on matrix 139. Similarly, head members 134 are mounted on the other matrix, following which matrix 139 with head members 133 and base member 7 are mounted, with dent points 137 directed downwards, on the other matrix; here, base member 7 holds head members 133 in matrix 139, preventing head members 133 from falling out of openings 140 in matrix 139. Matrix 139 is shifted under pressure in the direction of the of the other matrix, due to which fact dents 137 and 138 move toward one another, while piercing base member 7. Upon contact between head members 133 and 134, and opposite surfaces of base member 7, dents 138 of head members 134 are bent away to surfaces of head members 133, thereby fixing semimodules together and fastening modules on base member 7.

Modular applicator (FIG. 91) is composed of base member 7 of the applicator and modules with head members 141 shaped as triangles with fastening members in the form of triangular dents 142 formed by bent away apices of triangles, and needles shaped as three triangular dents 143 in each head member 141, said needles being cut out in the body of head member and bent away at the right angle in the direction opposite to dents 142. Dents 142 are passed through base member 7 and bent away to the surface thereof. Head members 141 are disposed on base member 7 in parallel rows 144 and in rows 145 that are perpendicular to rows 144 and are intersected by rows 144. In rows 144, one of every two adjacent head members 141 is disposed with its triangle base on the line where the other head member is disposed with its triangle apex. Gaps c are provided between rows 144, and gaps d, between adjacent head members in row 144. Magnitudes of gaps c and d have been selected from the condition of providing equal distances from each dent 143 (head members) to adjacent one, thereby ensuring uniform filling of base member 7 of the applicator with needles 143; this can be seen from the fact that needles 143 are disposed in the apices of equilateral triangles 146.

The highest degree of applicator flexibility is provided around axes disposed within gaps c.

This embodiment of the applicator features higher density of needles arrangement, higher strength and rigidity of brace between modules and base member 7 than the embodiment shown in FIG. 7, since each module is connected to base member 7 by means of three dents 142 that are stronger and more rigidly connected to head member 141.

Figure 92:
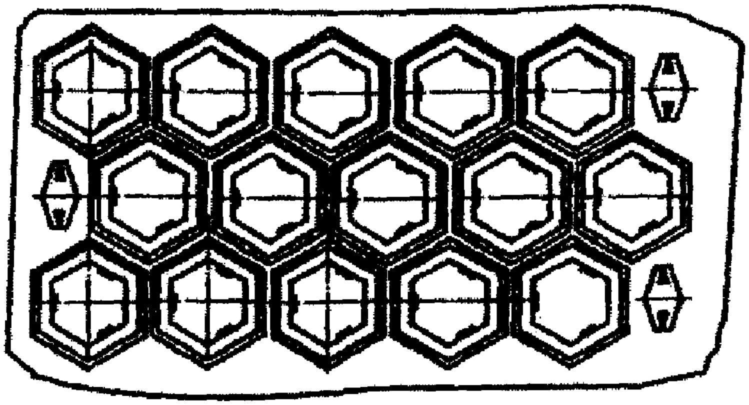
FIG. 92 is the diagram of arrangement, on the applicator base member, of modules shaped as triangles and provided with dents in the form of bent away triangle apices, and three dents made in the head member body, top view.

Modular applicator (FIG. 92) is composed of base member 7 and modules provided with hexagonal head members 147 with central hexagonal openings 148, fastening members shaped as triangular dents 149 formed by bent away triangular protrusions on the sides of openings 148, and needles shaped as three triangular dents 150 in each head member 147, cut out in the head member body and bent away at the right angle in the direction opposite to dents 149. Dents 149 (fastening members) are passed through base member 7 and bent away to the surface thereof. Head members 147 are arranged on base member 7 in parallel rows 152 that intersect with rows 151 . Modules with head members 153 are mounted along edges of base member 7 for the purpose of filling blank sections of base member 7 with needles of modules 147. These modules are shaped as rhombs with bent away pointed apices 154 that perform the function of fastening members, and with triangular dents 155 bent away therefrom, which perform the function of needles. Such arrangement of modules provides uniform filling with needles 150 and 155 of the total area of base member 7 since all needles 150 and 155 are disposed in the apices of equilateral triangles 156.

Figure 93:
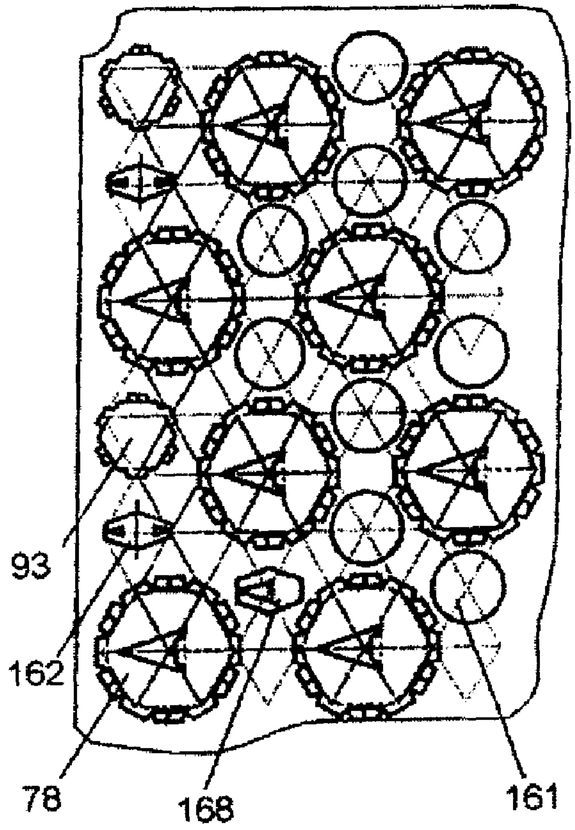
FIG. 93 is the diagram of arrangement, on the applicator base member, of modules shaped as hexagons provided with central openings with dents in the form of beams bent, away from the openings, and additional modules of a different shape, top view.
Figure 94:
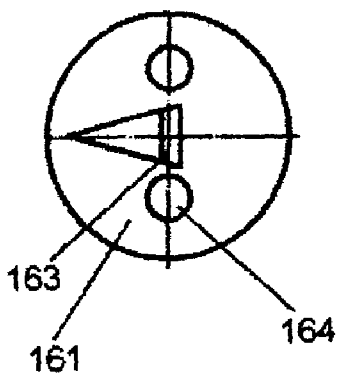
FIG. 94 shows a circular semimodule for the applicator of FIG. 93, provided with a needle and two openings for rivets, top view.
Figure 95:
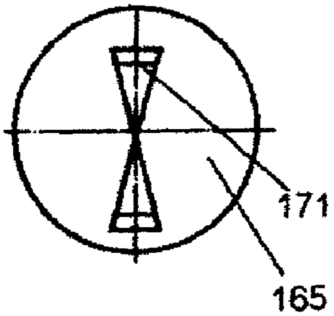
FIG. 95 demonstrates a circular semimodule with two openings for rivets, top view.
Figure 96:
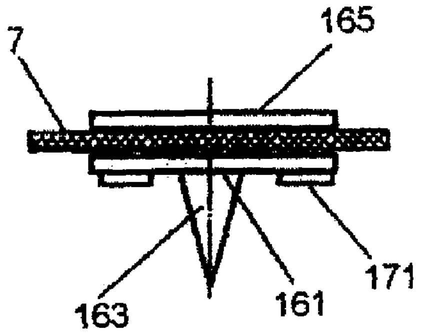
FIG. 96 is the diagram of mounting semimodules of FIGS. 94, 95 to the applicator base member, side view.
Figure 97:
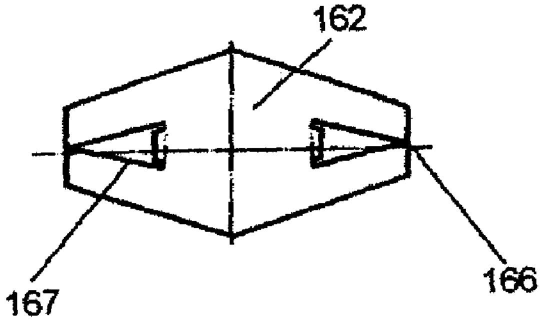
FIG. 97 shows a rhomb-shaped semimodule with two head members and two fastening members, top view.
Figure 98:
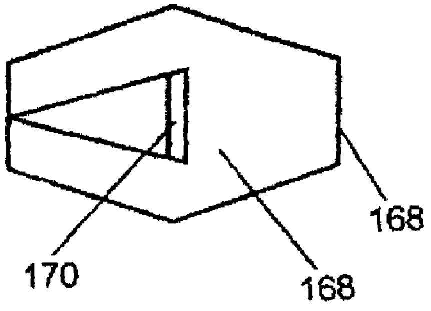
FIG. 98 demonstrates a rhomb-shaped module with one head member and two fastening members.

Modular applicator (FIG. 93) comprises base member 7 and modules composed by semimodules with circular head members 157. Some of these semimodules are provided with needles 158 shaped as several triangular dents formed by bent away triangular protrusions along periphery of head members 157 and bent away therefrom, and needles 159 shaped as triangular dents, one dent in each head member 157, said dents being cut out in the bodies of head members 157 and bent away therefrom at the right angle and in the same direction as needles 158. Other semimodules are provided with fastening members 160 that are passed through base member 7 and bent away to the surfaces of mating semimodules disposed on the opposite surface of base member 7. Head members 157 are disposed on base member 7 in parallel rows intersecting therebetween. Modules with circular head members 161 and rhomb-shaped head members 162 are mounted along edges of base member 7 and between said modules for the purpose of filling blank sections of base member 7 with needles of modules 157. Some of semimodules with circular head member 161 (FIGS. 94 through 96) are provided with needle 163 each, in the form of a triangular dent cut out in the body of head member 161 and bent away therefrom, and two openings 164 for fastening members 165 of a mating semimodule, shaped as two triangular dents cut out in the body of head member 161, passed through base member 7 and openings 164, and connecting both semimodules. Modules with rhomb-shaped head members 162 are made with bent away sharp apices that perform the function of needles 166, and triangular dents cut out in the body of head members 162 and bent away therefrom, said dents performing the function of fastening members 167.

It has to be noted that all the above geometrical figures (triangles, circles, polygons, and stars) used to make modules and semimodules, may be both regular and irregular.

Selection of specific shape for modules from the above-mentioned range depends on a required optimal combination of several applicator parameters: applicator flexibility, strength and rigidity of brace between applicator base member and dents, density of needles arrangement, uniformity, nonuniformity, or any other law of their distribution, comparative simplicity or complexity of technologies used for manufacture of modules and their fastening on the applicator base member. The required combination of applicator parameters, i.e. its flexibility, strength and rigidity of brace between applicator base member and dents, density of needles arrangement, uniformity, nonuniformity, or any other law of their distribution, is determined by the area and conditions of applicator use, e.g. the user's body part for which the applicator is intended. For example, circular head members with one needle and one fastening member disposed close to the center of such head member provide, in case of their staggered arrangement, a uniform filling of applicator with needles and higher flexibility of such applicator, thereby making the applicator especially suitable for reflexotherapy of user's body parts with curvilinear surfaces and small radii of curvature, e.g. extremities. This applicator however has a comparatively low density of needles and low rigidity of brace between modules and applicator base member. At the same time, circular or polygonal head members with needles and/or fastening members along their periphery or at a distance from such periphery provide maximum and uniform filling of applicator with needles, as well as higher rigidity of brace between modules and applicator base member, resulting however in its lower flexibility. This makes the use of such applicators expedient in cases of reflexotherapy of comparatively flat surfaces of the user's body, i.e. back, abdomen, or chest.

The invention claimed is:

1. A modular applicator for use in reflexotherapy comprising:

an elastic base member and metal modules fixed thereon and each module having a plurality of dents thereon;

each module including a head member with at least one of the plurality of dents defining a needle perpendicular thereto;

at least one of the plurality of dents defining a fastening member integral with the module head member of each module;

the fastening member or the needle together with the fastening member passing through the base member;

each module including two semimodules with the same shapes and sizes of head members, disposed one above another on opposite surfaces of the base member and fastened together;

each semimodule including some of the plurality of dents, the dents of at least one semimodule passing through the base member and through gaps between the dents of the other semimodule;

the gaps between the dents of each semimodule being sized such that there is base member material between adjacent dents; and the dents of each semimodule passing through the base member in opposite directions.

2. The modular applicator of claim 1, wherein:

said semimodules are shaped as two equilateral triangles with rectilinear or concave sides, and the plurality of dents are triangular dents formed by bent away apices of said equilateral triangles, a first of said equilateral triangles being turned with respect to a second of said equilateral triangles by an angle of 60 degrees.

3. The modular applicator of claim 1, wherein:

said semimodules are circular, oval or polygonal, and the plurality of dents are triangular dents protruding from an outer periphery of the head member.

4. The modular applicator of claim 1, wherein:

each semimodule includes a central opening and a some of the plurality of dents define needles shaped as triangular dents protruding from said central opening.

5. The modular applicator of claim 2, wherein:

the plurality of dents are cut out of and formed from said head member and bent therefrom at right angles.

* * * * *